United States Patent
Portnoy et al.

(10) Patent No.: US 10,774,390 B2
(45) Date of Patent: Sep. 15, 2020

(54) **METHODS AND COMPOSITIONS FOR MODULATING PRFA MEDIATED VIRULENCE GENE ACTIVATION IN *LISTERIA* SPP**

(71) Applicant: The Regents of the University of California, Oakland, CA (US)

(72) Inventors: Daniel A. Portnoy, Albany, CA (US); Jonathan L. Portman, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 128 days.

(21) Appl. No.: 15/754,288

(22) PCT Filed: Sep. 1, 2016

(86) PCT No.: PCT/US2016/050004
§ 371 (c)(1),
(2) Date: Feb. 21, 2018

(87) PCT Pub. No.: WO2017/040859
PCT Pub. Date: Mar. 9, 2017

(65) Prior Publication Data
US 2018/0237828 A1 Aug. 23, 2018

Related U.S. Application Data

(60) Provisional application No. 62/213,579, filed on Sep. 2, 2015.

(51) Int. Cl.
| | | |
|---|---|---|
| *A61K 39/02* | (2006.01) | |
| *C12Q 1/689* | (2018.01) | |
| *C07K 14/195* | (2006.01) | |
| *A61K 35/74* | (2015.01) | |
| *C12N 15/74* | (2006.01) | |
| *C12N 1/20* | (2006.01) | |
| *A61P 31/04* | (2006.01) | |
| *A61K 39/00* | (2006.01) | |

(52) U.S. Cl.
CPC .............. *C12Q 1/689* (2013.01); *A61K 35/74* (2013.01); *A61K 39/0208* (2013.01); *A61P 31/04* (2018.01); *C07K 14/195* (2013.01); *C12N 1/20* (2013.01); *C12N 15/74* (2013.01); *A61K 2039/521* (2013.01); *C12Q 2600/158* (2013.01)

(58) Field of Classification Search
None
See application file for complete search history.

(56) References Cited

U.S. PATENT DOCUMENTS

| 7,935,804 B2 | 3/2011 | Dubensky et al. |
| 2015/0125480 A1 | 5/2015 | Paterson et al. |

FOREIGN PATENT DOCUMENTS

| WO | WO2007/117371 A1 | 10/2007 |
| WO | WO2008/066774 A1 | 6/2008 |
| WO | WO2016/073585 A1 | 5/2016 |

OTHER PUBLICATIONS

Miner et al., Nov. 1, 2008 , vol. 154, No. 11, pp. 3579 3589 (Year: 2008).*
Reniere et al. , Nature, Jan. 8, 2015 , vol. 517, No. 7533, pp. 170-173. (Year: 2015).*
Reniere et al. Nature, Jan. 8, 2015 (Jan. 8, 2015), vol. 517, No. 7533, pp. 170-173. (Year: 2015).*
Miner et. al. Microbiology, Nov. 1, 2008 (Nov. 1, 2008), vol. 154, No. 11, pp. 3579 3589 (Year: 2008).*
Romick et al., Applied and Environonnental Microbiology, vol. 62, No. 1 ,pp. 304-307 1996. (Year: 1996).*
BD™ Tryptic Soy Broth (TSB) (Year: 2008).*
Deshayes et al. "Allosteric mutants show that PrfA activation is dispensable for vacuole escape but required for efficient spread and Listeria survival in vivo," Molecular Microbiology, Jun. 21, 2012 (Jun. 21, 2012), vol. 85, No. 3, pp. 461-477.
Miner et al. "Functional impact of mutational activation on the Listeria monocytogenes central virulence regulator PrfA," Microbiology, Nov. 1, 2008 (Nov. 1, 2008), vol. 154, No. 11, pp. 170-173.
Reniere et al. "Glutathione activates virulence gene expression of an intracellular pathogen," N

FIG. 2 (con't)

FIG. 2 (con't)

METHODS AND COMPOSITIONS FOR MODULATING PRFA MEDIATED VIRULENCE GENE ACTIVATION IN *LISTERIA* SPP

CROSS REFERENCE TO RELATED APPLICATIONS

Pursuant to 35 U.S.C. § 119 (e), this application claims priority to the filing date of the U.S. Provisional Patent Application Ser. No. 62/213,579, filed Sep. 2, 2015; the disclosure of which application is herein incorporated by reference.

ACKNOWLEDGMENT OF GOVERNMENT SUPPORT

This invention was made with Government support under award numbers AI027655 and AI063302 awarded by the National Institutes of Health. The Government has certain rights in the invention

INTRODUCTION

The use of vaccines is a cost-effective medical tool for the management of infectious diseases, including infectious diseases caused by bacteria, viruses, parasites, and fungi. In addition to effecting protection against infectious diseases, effort is also being expended to develop vaccines that stimulate the host's immune system to intervene in tumor growth.

Host immune responses include both the humoral immune response involving antibody production and the cell-mediated immune response. Protective immunization via vaccine has usually been designed to induce the formation of humoral antibodies directed against infectious agents, tumor cells, or the action of toxins. However, the control of certain diseases characterized by the presence of tumor cells or by chronic infection of cells with infectious agents, often requires a cell-mediated immune response either in place of, or in addition to, the generation of antibody. While the humoral immune response may be induced using live infectious agents and agents that have been inactivated, a cellular immune response is most effectively induced through the use of vaccines.

*Listeria monocytogenes* is a Gram-positive, food-borne human and animal pathogen responsible for serious infections in immunocompromised individuals and pregnant women. Severe *L. monocytogenes* infections in humans are characterized by meningitis, meningoencephalitis, septicemia, and fetal death. *L. monocytogenes* is ubiquitous in nature and, in addition, can be isolated from a wide variety of warm-blooded animals. *L. monocytogenes* elicits a predominantly cellular immune response when inoculated into an animal.

Recombinantly modified *L. monocytogenes* (Lm) vaccine platforms which are engineered to encode a designated antigen(s) relevant to a selected targeted pathogenic agent or malignancy have formed the basis for several human clinical trials. As *Listeria* can be a pathogenic organism, particularly in immunocompromised hosts, it is preferred that the administration step includes administering an attenuated *Listeria* that encodes an expressible, immunologically active portion of an antigen of interest. "Attenuation" refers to a process by which a bacterium is modified to lessen or eliminate its pathogenicity, but retains its ability to act as a prophylactic or therapeutic for the disease of interest. By way of example, genetically defined live-attenuated Lm ΔactAΔinlB, which is deleted of two virulence genes and is attenuated >3 logs in the mouse listeriosis model, retains its immunologic potency and has been shown to induce robust CD4 and CD8 T cell immunity in both mouse models of human disease as well as in humans, and has been shown to be safe and well-tolerated in clinical settings among patients with various solid tumor malignancies.

With respect to the mechanism of action of Lm vaccines, following administration to a subject and upon entry to the host cell cytosol, *Listeria monocytogenes* coordinates the expression of numerous essential virulence factors through activation of the Crp-Fnr family transcriptional regulator, PrfA. While much is known about PrfA and the virulence genes it regulates, the host-derived stimulus that leads to initial activation of PrfA remains unknown.

SUMMARY

Methods of assessing expression of a PrfA mediated expression construct in a Listerial host cell are provided. Aspects of the methods include maintaining a Listerial host cell that includes a PrfA mediated expression construct in a defined medium containing a reducing agent and evaluating expression of a product from the expression construct to assess expression of the PrfA mediated expression construct. Also provided are methods of producing and using a Listerial vaccine, as well as defined media for use in such methods.

BRIEF DESCRIPTION OF THE FIGURES

FIG. 1. Three strains of *Listeria monocytogenes* harboring a fluorescent reporter coding sequence driven by the actA promoter were grown in a chemically defined media with or without the addition of the noted reducing agents. In addition to the wild-type strain, a prfA-deletion strain, as well as a constitutively active prfA strain (written as prfA*), were tested in parallel as controls.

FIG. 2. In this experiment bacteria were grown in rich media (BHI) or *Listeria* synthetic media (LSM) with or without reducing agent (TCEP) and injected into mice IV. The data are CFUs at 48 in liver and spleens. WT bacteria and a PrfA* strain that has constitutively active PrfA were used. The data show that the bacteria grown in LSM plus TCEP have around 50-fold more bacteria in the organs showing that this method increases the virulence of the bacteria.

DETAILED DESCRIPTION

Methods of assessing expression of a PrfA mediated expression construct in a Listerial host cell are provided. Aspects of the methods include maintaining a Listerial host cell that includes a PrfA mediated expression construct in a defined medium containing a reducing agent and evaluating expression of a product from the expression construct to assess expression of the PrfA mediated expression construct. Also provided are methods of producing and using a Listerial vaccine, as well as defined media for use in such methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be constructed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, methods of evaluating PrfA mediated expression will be described first in greater detail, followed by a review of vaccines and methods of using the same according to embodiments of the invention.

Methods of Evaluating PrfA Mediated Expression

As summarized above, aspects of the invention include methods of assessing expression of a PrfA mediated expression construct in a *Listeria* host cell. As used herein the term "assessing" means characterizing in some manner, e.g., where the characterizing may be qualitative (e.g., detecting the occurrence of expression, identifying relative expression levels, etc.) or quantitative (e.g., measuring the expression in terms of copy number, etc.).

A PrfA mediated expression construct is a nucleic acid expression construct in which expression of a coding sequence of the construct is mediated, e.g., activated, by the presence of PrfA transcription activator. As such, PrfA mediated expression constructs include a PrfA responsive element, e.g., tTAACanntGTtAa (SEQ ID NO:01) having seven invariant nucleotides (in capitals) and a two-mismatch tolerance.

In addition to the PrfA responsive element, the expression constructs further include a coding sequence. In some instances, the coding sequence encodes a heterologous antigen. The heterologous antigen is, in certain embodiments, one that is capable of providing protection in an animal against challenge by the infectious agent from which the heterologous antigen was derived, or which is capable of affecting tumor growth and metastasis in a manner which is of benefit to a host organism. Heterologous antigens which may be encoded by the expression constructs thus include any antigen which when expressed by *Listeria* serves to elicit a cellular immune response which is of benefit to the host in which the response is induced. Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like. Heterologous antigens also include those which provide benefit to a host organism which is at risk for acquiring or which is diagnosed as having a tumor that expresses the said heterologous antigen(s). The host organism is may be a mammal, such as a human.

By the term "heterologous antigen," as used herein, is meant a protein or peptide, a glycoprotein or glycopeptide, a lipoprotein or lipopeptide, or any other macromolecule which is not normally expressed in *Listeria*, which substantially corresponds to the same antigen in an infectious agent, a tumor cell or a tumor-related protein. The heterologous antigen is expressed by an expression construct, and is processed and presented to cytotoxic T-cells upon infection of mammalian cells by the strain. The heterologous antigen expressed by *Listeria* species need not precisely match the corresponding unmodified antigen or protein in the tumor cell or infectious agent so long as it results in a T-cell response that recognizes the unmodified antigen or protein which is naturally expressed in the mammal. In other examples, the tumor cell antigen may be a mutant form of that which is naturally expressed in the mammal, and the antigen expressed by the *Listeria* species will conform to that tumor cell mutated antigen. By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens that may be introduced into *Listeria* by way of incorporating DNA encoding such antigens include any known or heretofore unknown tumor antigen. In other examples, the "tumor-related antigen" has no effect on tumor growth or metastasis, but is used as a component of the *Listeria* vaccine because it is expressed specifically in the tissue (and tumor) from which the tumor is derived. In still other examples, the "tumor-related antigen" has no effect on tumor growth or metastasis, but is used as a component of the *Listeria* vaccine because it is selectively expressed in the tumor cell and not in any other normal tissues.

The heterologous antigen useful in vaccine development may be selected using knowledge available to the skilled artisan, and many antigenic proteins which are expressed by tumor cells or which affect tumor growth or metastasis or which are expressed by infectious agents are currently known. For example, viral antigens which may be considered as useful as heterologous antigens include but are not limited to the nucleoprotein (NP) of influenza virus and the gag protein of HIV. Other heterologous antigens include, but are not limited to, HIV env protein or its component parts gp120 and gp41, HIV nef protein, and the HIV pol proteins, reverse transcriptase and protease. Still other heterologous antigens can be those related to hepatitis C virus (HCV), including but not limited to the E1 and E2 glycoproteins, as well as non-structural (NS) proteins, for example NS3. In addition, other viral antigens such as herpesvirus proteins may be useful. The heterologous antigens need not be limited to being of viral origin. Parasitic antigens, such as, for example, malarial antigens, are included, as are fungal antigens, bacterial antigens and tumor antigens.

As noted herein, a number of proteins expressed by tumor cells are also known and are of interest as heterologous antigens which may be inserted into the vaccine strain of the invention. These include, but are not limited to, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer. Other coding sequences of interest include, but are not limited to: costimulatory molecules, immunoregulatory molecules, and the like.

Additional heterologous antigens that may be encoded by the expression constructs are disclosed in WO2014106123, the disclosure of which is herein incorporated by reference.

In addition to the PrfA responsive element and the heterologous antigen coding sequence, the PrfA mediated expression construct may further include one or additional components from a *Listeria* virulence factor, such as but not limited to: promoter sequences, N-terminal coding sequences, etc., where such expression constructs may be referred to as virulence factor expression constructs. In virulence factor expression constructs, one or more regions or domains of the expression construct may be derived for a *Listeria* virulence factor, such as a PrfA mediated virulence factor. While such virulence factors may vary, examples of such virulence factors include, but are not limited to: Hly, Mpl, PICA, ActA, and PlcB.

In some instances, the PrfA mediated expression construction is an ActA expression construction that includes the ActA promoter and a coding sequence for the N-terminal domain of ActA fused to a heterologous antigen, i.e., a fusion proteins that includes an N-terminal domain of ActA fused to a heterologous antigen. The coding sequence for the N-terminal domain may encode an N-terminal domain that varies in length, ranging in some instances from 25 to 125 aa, such as 75 to 100 aa.

The Listerial host cell that includes the PrfA mediated expression construct, such as described above, may be any one of a number of different *Listeria* spp. *Listeria* spp of interest include, but are not limited to: *L. fleischmannii, L. grayi, L. innocua, L. ivanovii, L. marthii, L. monocytogenes, L. rocourtiae, L. seeligeri, L. weihenstephanensis,* and *L. welshimeri*. Thus, strains of *Listeria* other than *L. monocytogenes* may be host cells. In certain embodiments, the *Listeria* strain is *L. monocytogenes*.

In some instances, the *Listeria* host cell is attenuated. "Attenuation" and "attenuated" encompasses a *Listeria* host cell that is modified to reduce toxicity to a host. The host can be a human or animal host, or an organ, tissue, or cell. The *Listeria* host cell, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the LD50, the rate of clearance from an organ, or the competitive index (see, e.g., Auerbuch, et al. (2001) Infect. Immunity 69:5953-5957). Generally, an attenuation results an increase in the LD50 and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

A given *Listeria* host cell may include one or more modifications as compared to wildtype, which modifications provide for desirable qualities in the host cell, e.g., attenuation, enhanced immunogenicity, etc., and may be part of the PrfA mediated expression construct and/or another component of the Listerial host cell. Specific *Listeria* host cells that be assessed in embodiments of the invention include, but are not limited to, those described in PCT Published Application Nos.: WO 2014/106123; WO 2014/074635; WO 2009/143085; WO 2008027560 WO 2008066774; WO 2007117371; WO 2007103225; WO 2005071088; WO 2003102168; WO 2003/092600; WO/2000/009733; and WO 1999/025376; the disclosures of which applications are herein incorporated by reference.

As summarized above, aspects of the methods include maintaining a Listerial host cell comprising a PrfA mediated expression construct in a defined medium containing a reducing agent. By defined medium is meant a bacterial culture medium in which the exact chemical composition is known. As such, defined media that may be employed in methods of the invention are not complex media, i.e., they are not media in which the exact chemical constitution of the medium is not known. Defined media of interest may be non-naturally occurring media.

Defined media finding use in methods of the invention may vary. In some instances, the defined media includes a carbon source, e.g., glucose, one or more amino acids, e.g., L-Arginine, L-Histidine, DL-Isoleucine, L-Leucine, DL-Methionine, L-Phenylalanine, L-Tryptophan, DL-Valine, etc., a nitrogen source, e.g., adenine, one or more vitamins, e.g., Niacinamide/Nicotinamide D-Pantothenic Acid (hemi-calcium), Pyridoxal, Thiamine, etc.; one or more salts, e.g., $KH_2PO_4$, $Na_2HPO_4$, $MgSO_4$, etc.; and one or more trace metals, e.g., $FeCl_2$, $MnSO_4$, $ZnSO_4$, $CaCl_2$, $CuSO_4$, $CoCl_2$, H$_3$BO$_3$, Na$_2$MoO$_4$, NaCl, Sodium Citrate (Tri-Sodium Salt), etc; one or more essential nutrients, e.g., L-Cysteine, L-Glutamine; other (e.g., BRPL) components, e.g., Biotin, Riboflavin, Para-Aminobenzoic Acid, Lipoic Acid, etc., buffering agents, e.g., MOPS, HEPES, etc.; and the like. Specific defined growth media that may be employed methods of the invention include, but are not limited to: those described in: Whiteley, A. T., Pollock, A. J., & Portnoy, D. A. (2015). The PAMP c-di-AMP Is Essential for *Listeria* Growth in Rich but Not Minimal Media due to a Toxic Increase in (p)ppGpp. Cell Host and Microbe, 17(6), 788-798; and Phan-Thanh, L., & Gormon, T. (1997). A chemically defined minimal medium for the optimal culture of *Listeria*. International Journal of Food Microbiology, 35(1), 91-95; as well as the Experimental Section, below. While the ranges of various components of a defined media may vary, as desired, in some instances the defined media include one or more of: a carbon source, e.g., glucose, in an amount ranging from 0.01 to 0.10 M, such as 0.025 to 0.075 M; buffering agents, e.g., MOPS, in an amount ranging from 0.05 to 0.2 M, such as 0.075 to 0.125 M; one or more salts, where the amount of any given salt may vary, ranging in some instances from 0.001 to 0.05 M, such as 0.001 to 0.02 M; BRPL components, where the amount of any given BRPL component may vary, ranging in some instances from 0.01 to 10 μm, such as 0.02 to 7.5 μm; an amino acid component made up of one or more amino acids, where the amount of any given amino acid may vary, ranging in some instances from 0.0001 to 0.0020 M, such as 0.0004 to 0.0010 M; a vitamin component made up of one or more amino acids, where the amount of any given amino acid may vary, ranging in some instances from 1 to 10 μm, such as 2.5 to 9 μm; a nitrogen source, e.g., adenine, ranging from 15 to 25 μm, such as 17.5 to 20 μm; a trace metal component made up of one or more trace metals, where the amount of any given trace metal may vary, ranging in some instances from 0.05 to 150 μm, such as 0.1 to 100 μm; and an essential nutrient component made up of one or more essential nutrients, e.g., L-Cysteine and/or L-Glutamine, wherein the amount of any given essential nutrient may vary, ranging in some instances from 500 to 5000 μm, such as 500 to 4500 μm.

As summarized above, the defined media employed in methods of the invention further include a reducing agent. The reducing agent may be provided in the media as the reducing agent itself or biochemical precursors thereof. Reducing agents that may be provided in the growth medium include, but are not limited to: glutathione (GSH), 2-mercaptoethanol (BME), dithiothreitol (DTT), dithioerythritol (DTE) tris(2-carboxyethyl)phosphine (TCEP), tris(3-hydroxypropyl)phosphine (THP), cysteine, cysteamine and combinations thereof. The concentration of reducing agent that is provided in the defined growth media may vary so long as it is effective to result in PrfA activation of expression of responsive virulence factors in the host cell (i.e., is present in a PrfA activating amount), wherein in some instances the concentration ranges from 1 to 20 mM, such as 1.5 to 15 mM, e.g., 1.5 to 20 mM, such as 2 to 10 mM.

In practicing methods of the invention, the *Listeria* host cell is maintained in the defined growth media under conditions and for a time sufficient for PrfA mediated expression from the target PrfA mediated expression construct to occur. In some instances, the host cell is maintained in the defined medium at a temperature ranging from 4° C. to 40° C., such as from 15° C. to 40° C., e.g., 25° C. to 40° C., such as 35° C. to 37° C. While the period of time during which the host cell is maintained in the conditions may vary, in some instances the period of time ranges from 30 mins to 72 hours, e.g., 1 hour to 48 hours, including 6 hours to 24 hours.

As summarized above, aspects of the methods further include evaluating expression of a product from the expression construct to assess expression of the PrfA mediated expression construct and/or secretion of the expression product from the host cell. The evaluation may be accomplished using any convenient protocol, e.g., by assaying for the presence of the product encoded by the expression product, where the assaying may be qualitative (e.g., where the presence or absence is determined), semi-quantitative (e.g., where a relative amount is determined) or quantitative (e.g., where an absolute amount is determined), as desired. As such, methods of the invention may include detecting an expression product of the expression construct of interest in the medium that includes the host cell. The expression product of interest may be detected using any convenient protocol, e.g., nucleic acid detection protocol, protein detection protocol, etc. In some instances, a detection protocol may include contacting the assay medium, e.g., that includes the host cell or components thereof, where the host cell may be modified to provide for detection, e.g., permeabilized or lysed, with a labeled binding member that specifically binds to the expression product. The nature of the labeled binding member may vary in terms of binding moiety and detectable label, where binding moieties of interest include nucleic acids and peptides/proteins, e.g., antibodies and binding fragments thereof; and label moieties may also vary, where examples include, but are not limited to, fluorescent labels, mass labels, isotopic labels, etc.

In some instances, the methods further include comparing the results of the evaluation, e.g., an observed expression level, an amount of secreted product, etc., to a threshold value. In such instances, the method may further include identifying the *Listeria* host cell as an acceptable vaccine if the observed results exceed the threshold value.

Vaccines

Bacteria identified by methods as described above or produced using the defined media as described above find use as, among other things, vaccines. The bacteria may be live or Killed But Metabolically Active ("KBMA"). KBMA vaccine strains are constructed by abrogating the capacity for nucleotide excision repair through deletion of DNA repair genes such as uvrA and uvrB. The gene deletion renders the bacteria sensitive to photochemical inactivation through the combined treatment of psoralens and UVA. Because of their inability to repair the psoralen-induced DNA cross-links formed, KBMA bacterial strains are unable to replicate and are thus functionally noninfectious. This characteristic provides an improved safety profile in comparison to live attenuated strains. The very limited number of cross-links, however, preserves their metabolic activity, including antigen expression, and thus their immune potential. KBMA vaccine strains are described in U.S. Pat. No. 7,833,775, the disclosure of which is herein incorporated by reference.

Such vaccines may be administered to a vertebrate by contacting the vertebrate with a sublethal dose of the bacteria, where contact may include administering the vaccine to the host. In some embodiments, the bacteria are provided in a pharmaceutically acceptable formulation. Administration can be oral, parenteral, intranasal, intramuscular, intradermal, intraperitoneal, intravascular, subcutaneous, direct vaccination of lymph nodes, administration by catheter or any one or more of a variety of well-known administration routes. In farm animals, for example, the vaccine may be administered orally by incorporation of the vaccine in feed or liquid (such as water). It may be supplied as a lyophilized powder, as a frozen formulation or as a component of a capsule, or any other convenient, pharmaceutically acceptable formulation that preserves the antigenicity of the vaccine. Any one of a number of well known pharmaceutically acceptable diluents or excipients may be employed in the vaccines of the invention. Suitable diluents include, for example, sterile, distilled water, saline, phosphate buffered solution, and the like. The amount of the diluent may vary widely, as those skilled in the art will recognize. Suitable excipients are also well known to those skilled in the art and may be selected, for example, from A. Wade and P. J. Weller, eds., *Handbook of Pharmaceutical Excipients* (1994) The Pharmaceutical Press: London. The dosage administered may be dependent upon the age, health and weight of the patient, the type of patient, and the existence of concurrent treatment, if any. The vaccines can be employed in dosage forms such as capsules, liquid solutions, suspensions, or elixirs, for oral administration, or sterile liquid for formulations such as solutions or suspensions for parenteral, intranasal intramuscular, or intravascular use. In accordance with the invention, the vaccine may be employed, in combination with a pharmaceutically acceptable diluent, as a vaccine composition, useful in immunizing a patient against infection from a selected organism or virus or with respect to a tumor, etc. Immunizing a patient means providing the patient with at least some degree of therapeutic or prophylactic immunity against selected pathogens, cancerous cells, etc.

The subject vaccines find use in methods for eliciting or boosting a cellular immune response, e.g., a helper T cell or a cytotoxic T-cell response to a selected agent, e.g., pathogenic organism, tumor, etc., in a vertebrate, where such methods include administering an effective amount of the *Listeria* vaccine. The subject vaccines find use in methods for eliciting in a vertebrate an innate immune response that augments the antigen-specific immune response. Furthermore, the vaccines of the present invention may be used for treatment post-exposure or post diagnosis. In general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure. As such, the subject vaccines prepared with the subject vectors find use as both prophylactic and therapeutic vaccines to induce immune responses that are specific for antigens that are relevant to various disease conditions.

The patient may be any human and non-human animal susceptible to infection with the selected organism. The subject vaccines find use with vertebrates, including mammals, such as primates, e.g., humans, and with domestic animals. Domestic animals include domestic fowl, bovine, porcine, ovine, equine, caprine, Leporidate (such as rabbits), or other animal which may be held in captivity.

The subject vaccines find use in vaccination applications as described in PCT Published Application Nos.: WO 2014/106123; WO 2014/074635; WO 2009/143085; WO 2008027560 WO 2008066774; WO 2007117371; WO 2007103225; WO 2005071088; WO 2003102168; WO 2003/092600; WO/2000/009733; and WO 1999/025376; the disclosures of which applications are herein incorporated by reference.

The following examples are offered by way of illustration and not by way of limitation.

EXPERIMENTAL

I. Reducing Agent Mediated PrfA Activation

Upon entry to the host cell cytosol, *Listeria monocytogenes* coordinates the expression of numerous essential virulence factors through activation of the Crp-Fnr family transcriptional regulator, PrfA. While much is known about PrfA and the virulence genes it regulates, the host-derived stimulus that leads to initial activation of PrfA remains unknown. Recently it has been shown that both host and bacterially synthesized glutathione is required for the activation of PrfA in tissue culture and animal models (Reniere, M. L., Whiteley, A. T., Hamilton, K. L., John, S. M., Lauer, P., Brennan, R. G. & Portnoy, D. A. Glutathione activates virulence gene expression of an intracellular pathogen. Nature 517, 170-173 (2015)), however exogenous glutathione is insufficient to stimulate PrfA activation in standard complex broth culture.

Experiments were conducted to identify any additional factors required for PrfA activation. When *L. monocytogenes* was grown in a chemically defined media (but not rich (i.e., complex) media), an excess of exogenously added glutathione was now sufficient to stimulate activation of PrfA. Further studies revealed that this activation of PrfA in vitro was not specific to glutathione, but could be recapitulated by an array of reducing agents including 2-mercaptoethanol (BME), dithiothreitol (DTT), and tris(2-carboxyethyl)phosphine (TCEP). In the absence of an unknown inhibitory compound(s) found in rich (i.e., complex) growth media, the host-derived stimulus sensed by *L. monocytogenes* to activate PrfA is simply the highly reducing redox state of the host-cell cytosol itself. This finding addresses a critical, outstanding question in the *L. monocytogenes* field, and provides a simple mechanism for how an intracellular pathogen is able to distinguish the host cell cytoplasm from other cellular compartments.

This discovery is the identification of in vitro growth conditions to stimulate expression of ActA. Three different strains were employed: WT 10403S (Lauer et al., J. Bacteriol. (2002) 184:4177-4186; ΔprfA which was an in frame deletion in prfA made by allelic exchange; and PrfA* which has a G145S mutation. The strains were engineered to express TagRFP from the actA promoter (e.g., as reported in Waite et al., PLoS Pathog. (2011)$_7$:e1001326. A chemically defined media detailed in Table 1 was prepared.

TABLE 1

| Stock Name | Ingredient | Vendor | Catalog | Final Concentration (M) (µM) |
|---|---|---|---|---|
| MOPS | MOPS | Sigma | M3183-500G | 0.1000 |
| Glucose | Glucose | Sigma | G8270-1KG | 0.0555 |
| Phosphate | KH2PO4 | Sigma | P5379-500G | 0.0048 |
| | Na2HPO4•7H2O | Sigma | S2429-1KG | 0.0115 |

TABLE 1-continued

| Stock Name | Ingredient | Vendor | Catalog | Final Concentration (M) (μM) |
|---|---|---|---|---|
| MgSO4 | MgSO4•7H2O | EMD Chemical | MX0070-1 | 0.0017 |
| BRPL | Biotin | Sigma | B-4501 | (2.05) |
|  | Riboflavin | Sigma | R9504-25G | (1.33) |
|  | Para-Aminobenzoic Acid | Sigma | A-9878 | (7.29) |
|  | Lipoic Acid | Sigma | T56215-1G | (0.02) |
| Amino-acids | L-Arginine•HCl | Sigma | A5131-25G | 0.0005 |
|  | L-Histidine•HCl•H2O | Sigma | H8125-25G | 0.0005 |
|  | DL-Isoleucine | Sigma | 298689-50G | 0.0008 |
|  | L-Leucine | Sigma | L602-100G | 0.0008 |
|  | DL-Methionine | Sigma | M9500 | 0.0007 |
|  | L-Phenylalanine | Sigma | P2126-100G | 0.0006 |
|  | L-Tryptophan | Sigma | T0254-25G | 0.0005 |
|  | DL-Valine | Sigma | V-0375 | 0.0009 |
| Vitamins | Niacinamide/Nicotinamide | Sigma | N3376-100G | (8.19) |
|  | D-Pantothenic Acid (hemicalcium) | Sigma | P5710-25G | (4.20) |
|  | Pyridoxal•HCl | Sigma | P9130-5G | (4.91) |
|  | Thiamine•HCl | Sigma | T4562-25G | (2.96) |
| Adenine | Adenine | Acros Organics | 147440250 | (18.50) |
| Trace Metals | FeCl2•4H2O | Sigma | 44939-50G | 5 |
|  | MnSO4•H2O | Sigma | 221287-100G | 50 |
|  | ZnSO4•7H2O | Sigma | Z0251-100G | 1 |
|  | CaCl2•2H2O | EMD Chemical | CX0130-2 | 10 |
|  | CuSO4•5H2O | Sigma | C-7631 | 0.1 |
|  | CoCl2•7H2O | Baker | 1696 | 0.1 |
|  | H3BO3 | Fisher | BP168-500 | 0.1 |
|  | Na2MoO4•2H2O | Sigma | M-1003 | 0.1 |
|  | NaCl | Fisher | S271-3 | 0.0086 |
|  | Sodium Citrate (Tri-Sodium Salt) | Fisher | S279-3 | 100 |
| Added | L-Cysteine•2HCl | Sigma | C-1276 | (634.44) |
| Fresh | L-Glutamine | Sigma | G3126-100G | (4105.65) |

Next, a number of reducing agents listed in Table 2 were added to the media.

TABLE 2

| Reducing agent tested | Optimal concentration for prfA activation |
|---|---|
| 2-mercaptoethanol (BME) | 2 mM |
| dithiothreitol (DTT) | 2 mM |
| tris(2-carboxyethyl)phosphine (TCEP) | 2 mM |
| L-Cysteine | 10 mM |
| Glutathione (reduced) | 10 mM |

Figure 1:
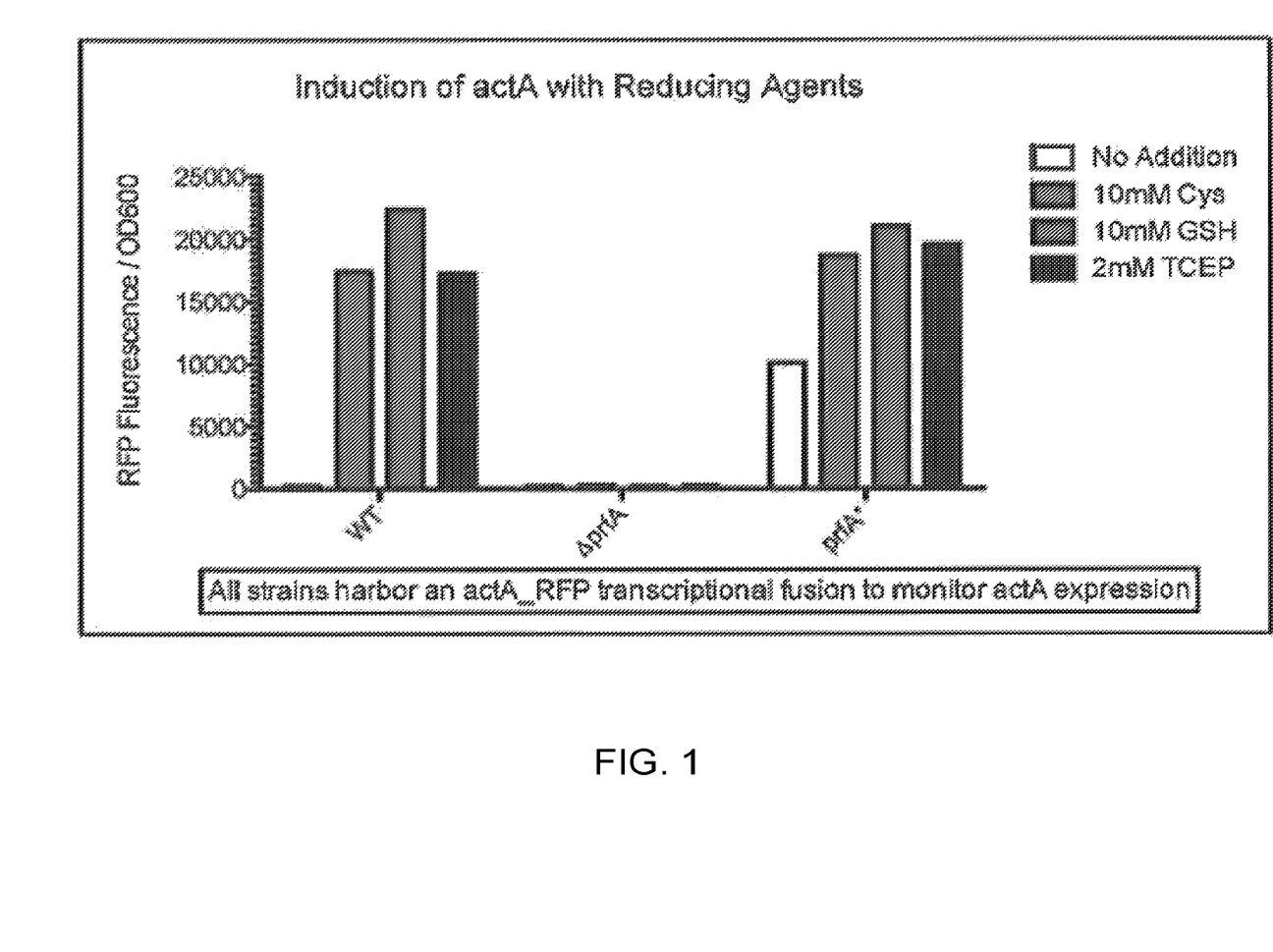

The three strains were grown in the chemically defined media with or without the addition of the noted reducing agents. In addition to the wild-type strain, the prfA-deletion strain and the constitutively active prfA strain (written as prfA*) were tested in parallel as controls. FIG. 1 shows an example of induction of ActA using three different reducing agents, (L-Cysteine, Glutathione and TCEP).

The above method allows for easy testing of prfA-controlled expression constructs for expression and secretion without the need to infect cells. In some instances, the method increases immunogenecity of vaccine vectors. In some instances the method increases the immunogenicity of Killed but Metabolically Active (KBMA) *Listeria* vaccines.

II. Immunogenicity of Strains Grown in Rich Media, Defined Media, and Defined Media Including a PrfA Activating Amount of Reducing Agent.

The wild type, ΔprfA and PrfA* strains of the above example are modified to contain an Ag expression cassette encoding five defined H-2b-restricted major histocompatibility complex (MHC) class I epitopes that have previously been shown to elicit a range of CD8+ T-cell responses in mice, when encoded by live-attenuated Lm ΔactA/ΔinlB, and KBMA vaccines (Lauer et al., Infect. Immun. (2008) 76: 3742-3753). The use of an array of precise class I restricted epitopes provides an optimized method for assessing immunogenicity in vivo, simplifying comparisons of the strains grown under different conditions.

The Ag expression cassette construct encodes four tandemly spaced vaccinia virus (A42R, C4L, K3L, and B8R) class I epitopes and the chicken OVA (SL8) epitope, and was synthesized and then cloned under the control of the PrfA-regulated actA promoter as a fusion protein with the 100 N-terminal amino acids of ActA (Lauer et al., 2008). The construct is known as Quadvac and is cloned into a derivative of the pPL2 integration vector and then integrated into the tRNAArg site of the wild type, ΔPrfA and PrfA* *Listeria* strains (Lauer et al., 2002; Lauer et al., 2008). Additionally, the wild type, ΔprfA and PrfA* strains of the above example are modified to contain a different antigen expression cassette that consists of the prfA-dependent actA promoter, ActAN100, and human mesothelin, which contains an overlapping library of multiple balb/c restricted T cell epitopes that has been shown to be effective in preclinical models and human clinical trials. See Le et al., J. Clin. Oncol. (2015) 33:1325-33.

These modified strains are grown under the conditions of the previous example, and also in a rich (i.e., complex) media culture. To evaluate relative immunogenicity of Quadvac expressing strains, groups of 5 female C57BL/6 (H-2b) mice are immunized twice at an interval of 36 days with the wild type, ΔPrfA and PrfA* *Listeria* strains each encoding Quadvac and each grown in rich media culture, or under the conditions as described in the above example, at a dose level of 5×106 colony forming units (CFU). Six days following the second immunization, spleens are harvested from vaccinated mice, and the magnitude of the CD8+ T cell responses specific for the 5 encoded epitopes is measured by ELISpot analysis of splenocytes following overnight stimulation with 1 µM of peptides corresponding to each of the MHC class I epitopes having the amino acid sequence as follows, as described previously: A42R88-96, YAPVSPIVI; C4L125-132, LNFRFENV; K3L6-15, YSLPNAGDVI; B8R20-27, TSYKFESV; and, SL8257-264, SIINFEKL (Lauer et al., 2008; Moutaftsi et al., Nat Biotechnol (2006) 24: 817-819). To evaluate the relative immunogenicity of mesothelin expressing strains, groups of 5 female balb/c mice are immunized once or twice with 5×106 cfu. Seven days after the prime or 6 days post boost, ELISpot analysis of splenocytes is performed using an overlapping mesothelin peptide pool. This demonstrates the immunogenicity of the wild type and PrfA* strains grown in defined media containing a PrfA activating amount of reducing agent.

III. Virulence of Strains Grown in Rich Media, Defined Media, and Defined Media Including a PrfA Activating Amount of Reducing Agent Prior to infection, bacterial strains were grown to stationary phase overnight in *Listeria* Synthetic Media (LSM) at 37° C., then diluted into either BHI or LSM, with or without reducing agent (2 mM TCEP) and grown at 37° C. with shaking until the OD600 was approximately 0.5. Cultures were re-suspended in 1× phosphate-buffered saline (PBS) and used to intravenously infect female CD-1 mice between 6 and 8 weeks of age with a final inoculum of $10^5$ bacteria. At 48 hrs post-infection, mice were sacrificed and organs collected. Bacterial burdens were enumerated by plating organ homogenates on LB plates and incubating overnight.

Figure 2:
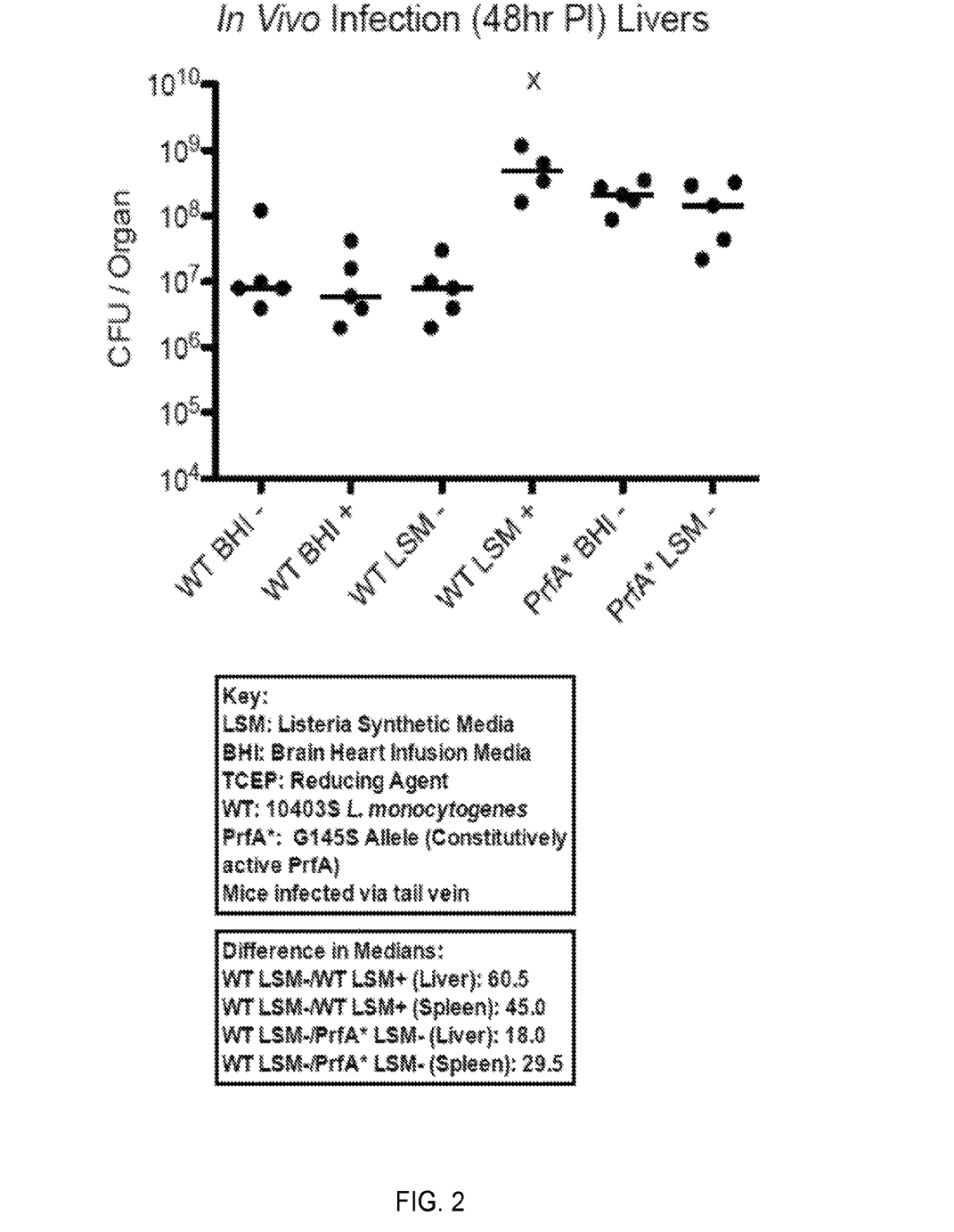

The results are shown in FIG. 2. WT bacteria and a PrfA* strain that has constitutively active PrfA were used. Specifically, the data shown in the two main panels demonstrates that in the presence of the defined medium and TCEP, *Listeria* exhibits an activation of PrfA-dependent expression equivalent to that of a PrfA-constituitive mutant, which activation is measured by virulence. The smaller figure indicates that the observed effect is not due to the initial bacterial dosage. The data show that the bacteria grown in LSM plus TCEP have around 50-fold more bacteria in the organs showing that this method increases the virulence of the bacteria.

Notwithstanding the appended clauses, the disclosure is also defined by the following clauses:

1. A method of assessing expression of a PrfA mediated expression construct, the method comprising:
maintaining a Listerial host cell comprising a PrfA mediated expression construct in a defined medium containing a PrfA activating amount of a reducing agent; and
evaluating expression of a product from the expression construct to assess expression of the PrfA mediated expression construct.
2. The method according to Clause 1, wherein the PrfA mediated expression construct is a modified virulence factor expression construct.
3. The method according to any of Clauses 1 to 2, wherein the modified virulence factor expression construct is an ActA expression construct.
4. The method according to Clause 3, wherein the ActA expression construct comprises the ActA promoter.
5. The method according to Clause 4, wherein the ActA expression construction encodes a fusion protein.
6. The method according to Clause 5, wherein the fusion protein comprises an N-terminal ActA domain.
7. The method according to any of the preceding clauses, wherein the PrfA mediated expression construct encodes a heterologous antigen.
8. The method according to any of the preceding clauses, wherein the reducing agent is selected from the group consisting of: glutathione (GSH), 2-mercaptoethanol (BME), dithiothreitol (DTT), cysteine and tris(2-carboxyethyl)phosphine (TCEP) and combinations thereof.
9. The method according to any of the preceding clauses, wherein the defined medium comprises a carbon source, one or more amino acids, a nitrogen source, one or more vitamins, one or more salts and one or more trace metals.
10. The method according to Clause 9, wherein the carbon source comprises glucose and the nitrogen source comprises adenine.
11. The method according to any of the preceding clauses, wherein the assessing comprises comparing an observed expression level to a threshold value.
12. The method according to Clause 11, wherein the method further comprises identifying the Listerial host cell as an acceptable vaccine if the observed expression level exceeds the threshold value.
13. The method according to any of the preceding clauses, wherein the Listerial host cell is *Listeria monocytogenes*.
14. A method of producing a vaccine, the method comprising culturing a Listerial host cell comprising a PrfA mediated expression construct encoding a heterologous antigen in a defined growth medium comprising a PrfA activating amount of a reducing agent in a manner sufficient to produce a vaccine.
15. The method according to Clause 14, wherein the PrfA mediated expression construct is a modified virulence factor expression construct.
16. The method according to Clause 15, wherein the modified virulence factor expression construct is an ActA expression construct.
17. The method according to Clause 16, wherein the ActA expression construct comprises the ActA promoter.
18. The method according to Clause 17, wherein the ActA expression construction encodes a fusion protein.
19. The method according to Clause 18, wherein the fusion protein comprises an N-terminal ActA domain.
20. The method according to any of Clauses 14 to 19, wherein the reducing agent is selected from the group consisting of: glutathione (GSH), 2-mercaptoethanol (BME), dithiothreitol (DTT), cysteine and tris(2-carboxyethyl)phosphine (TCEP) and combinations thereof.
21. The method according to any of the preceding clauses, wherein the defined medium comprises a carbon source, one or more amino acids, a nitrogen source, one or more vitamins, one or more salts and one or more trace metals.
22. The method according to Clause 21, wherein the carbon source comprises glucose and the nitrogen source comprises adenine.
23. The method according to any of Clauses 14 to 22, wherein the Listerial host cell is *Listeria monocytogenes*.
24. The method according to any of Clauses 14 to 22, wherein the method further comprises killing the Listerial host.
25. A vaccine comprising *Listeria* bacteria identified according to the method of Clause 12 or produced according to the method of any of Clauses 14 to 24.
26. The vaccine according to Clause 25, wherein the *Listeria* bacteria are attenuated.
27. The vaccine according to Clause 25, wherein the *Listeria* bacteria are KBMA.
28. A method of eliciting or boosting a cellular immune response in a subject to an antigen, the method comprising administering to said subject an effective amount of a vaccine according to any of Clauses 25 to 27.
29. A defined bacterial culture medium comprising a PrfA activating amount of a reducing agent.

30. The culture medium according to Clause 29, wherein the reducing agent is selected from the group consisting of: glutathione (GSH), 2-mercaptoethanol (BME), dithiothreitol (DTT), cysteine and tris(2-carboxyethyl)phosphine (TCEP) and combinations thereof.

31. The culture medium according to any of Clauses 29 to 30, wherein the defined medium comprises a carbon source, one or more amino acids, a nitrogen source, one or more vitamins, one or more salts and one or more trace metals.

32. The culture medium according to Clause 31, wherein the carbon source comprises glucose and the nitrogen source comprises adenine.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of assessing expression of a PrfA mediated expression construct, the method comprising:
maintaining a Listerial host cell comprising a PrfA mediated expression construct in a defined medium containing a PrfA activating amount of a reducing agent; and
evaluating expression of a product from the expression construct to assess expression of the PrfA mediated expression construct.

2. The method according to claim 1, wherein the PrfA mediated expression construct is a modified virulence factor expression construct.

3. The method according to claim 1, wherein the modified virulence factor expression construct is an ActA expression construct.

4. The method according to claim 3, wherein the ActA expression construct comprises the ActA promoter.

5. The method according to claim 4, wherein the ActA expression construction encodes a fusion protein.

6. The method according to claim 5, wherein the fusion protein comprises an N-terminal ActA domain.

7. The method according to claim 1, wherein the PrfA mediated expression construct encodes a heterologous antigen.

8. The method according to claim 1, wherein the assessing comprises comparing an observed expression level to a threshold value.

9. The method according to claim 1, wherein the Listerial host cell is *Listeria monocytogenes*.

10. The method according to claim 1, wherein the defined medium is not a brain heart infusion medium or a tryptic soy broth medium.

* * * * *